(12) United States Patent
Swanson

(10) Patent No.: US 8,271,099 B1
(45) Date of Patent: Sep. 18, 2012

(54) IMPLANTABLE PADDLE LEAD COMPRISING COMPRESSIVE LONGITUDINAL MEMBERS FOR SUPPORTING ELECTRODES AND METHOD OF FABRICATION

(75) Inventor: John Swanson, Portland, OR (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 261 days.

(21) Appl. No.: 12/729,611

(22) Filed: Mar. 23, 2010

Related U.S. Application Data

(60) Provisional application No. 61/162,596, filed on Mar. 23, 2009.

(51) Int. Cl.
*A61N 1/00* (2006.01)

(52) U.S. Cl. ........................................................ 607/117

(58) Field of Classification Search ........... 607/115–156
See application file for complete search history.

(56) References Cited

U.S. PATENT DOCUMENTS

| | | |
|---|---|---|
| 5,000,194 A | 3/1991 | van den Honert et al. |
| 5,800,500 A | 9/1998 | Spelman et al. |
| 6,374,143 B1 | 4/2002 | Berrang et al. |
| 6,415,187 B1 | 7/2002 | Kuzma et al. |
| 7,085,605 B2 | 8/2006 | Bluger et al. |
| 7,177,702 B2 | 2/2007 | Wallace et al. |
| 2002/0022873 A1 | 2/2002 | Erickson et al. |
| 2003/0040785 A1 | 2/2003 | Maschino et al. |
| 2005/0154435 A1 | 7/2005 | Stern et al. |
| 2005/0288758 A1 | 12/2005 | Jones et al. |
| 2007/0191709 A1 | 8/2007 | Swanson |
| 2007/0265691 A1 | 11/2007 | Swanson |
| 2010/0082086 A1* | 4/2010 | Zhu .............................. 607/117 |
| 2010/0114278 A1 | 5/2010 | McMorrow et al. |

* cited by examiner

*Primary Examiner* — Scott Getzow
(74) *Attorney, Agent, or Firm* — Craig Hoersten; Christopher S. L. Crawford; Peter R. Lando

(57) ABSTRACT

In one embodiment, a paddle-style lead for implantation in the epidural space, the paddle-style lead comprising: a paddle structure that comprises a frame of rigid material, the frame comprising first, second, and third longitudinal members, a distal linking portion that is mechanically coupled to the first, second, and third longitudinal members, and a proximal linking portion that is mechanically coupled to the first, second, and third longitudinal members; wherein a respective plurality of electrodes are provided for each of the first, second, and third longitudinal members, each plurality of electrodes being electrically coupled to conductors of a lead body; wherein the distal and proximal linking portions are adapted to permit compression of the first and third longitudinal members toward each other and to permit the second longitudinal member to move out of plane relative to the first and third longitudinal members when a compressive force is applied to the paddle.

20 Claims, 7 Drawing Sheets

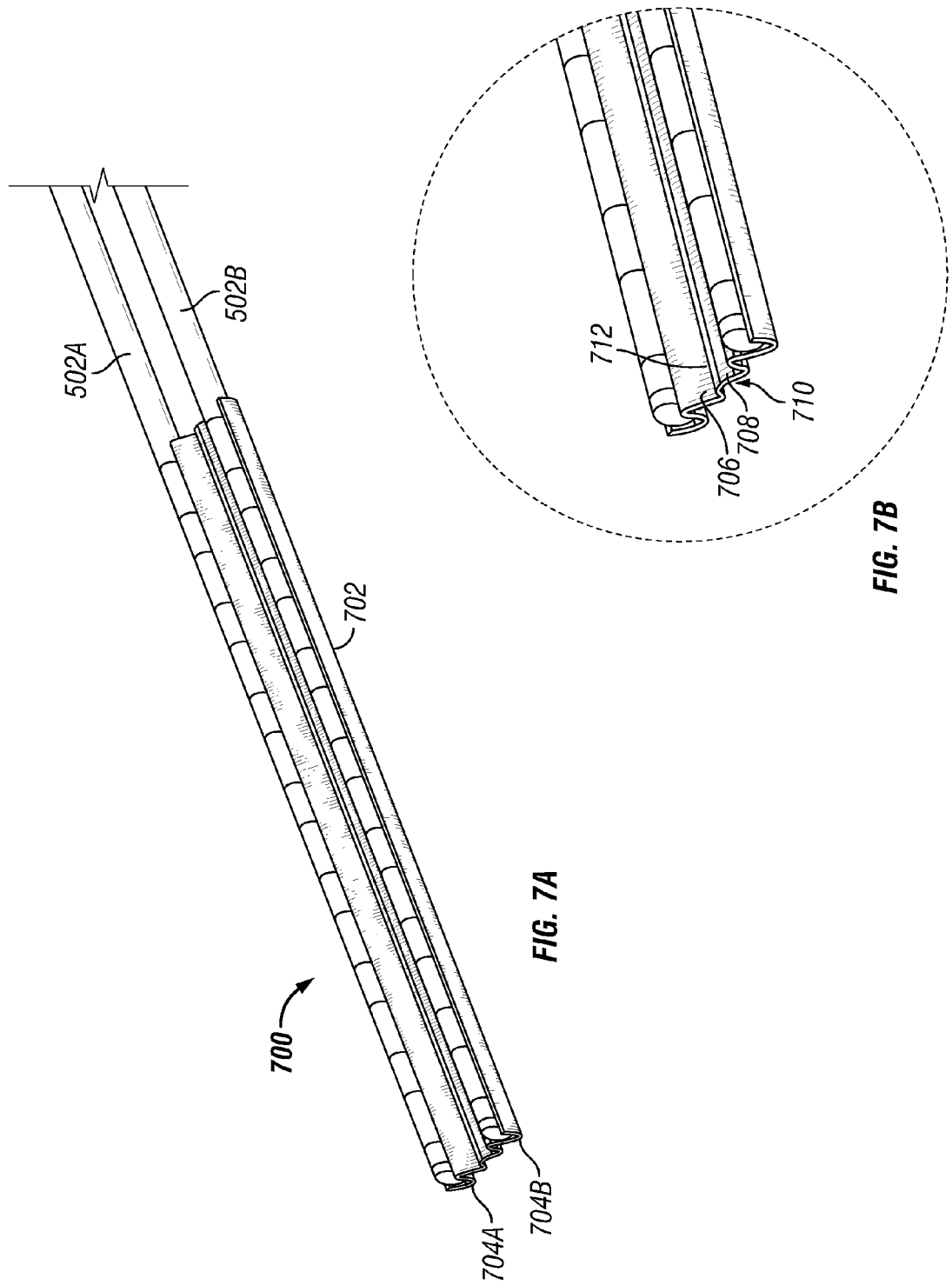

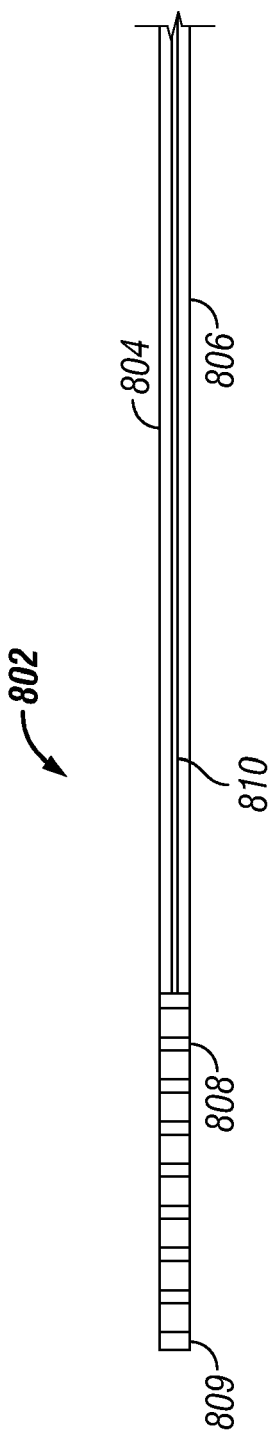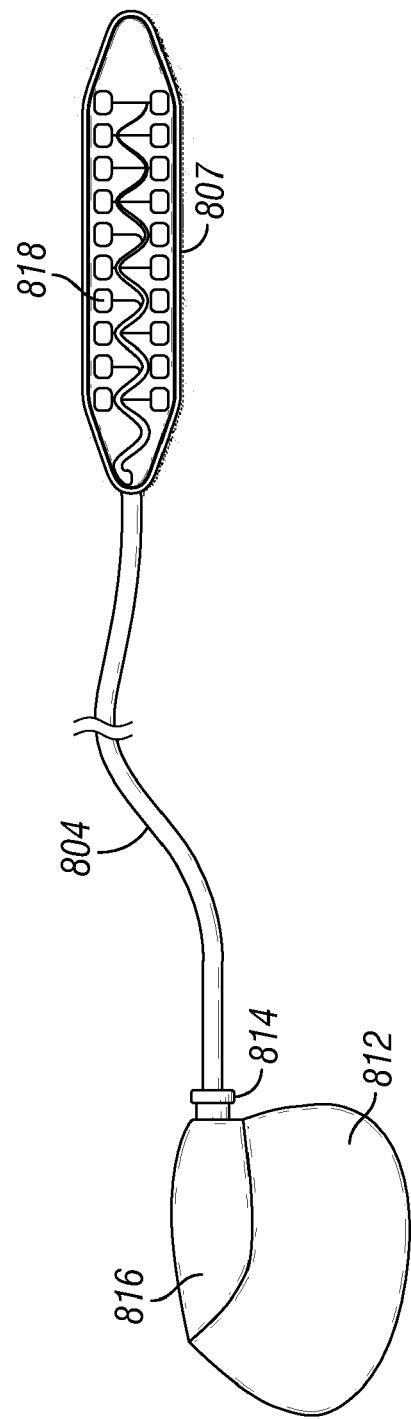

IMPLANTABLE PADDLE LEAD COMPRISING COMPRESSIVE LONGITUDINAL MEMBERS FOR SUPPORTING ELECTRODES AND METHOD OF FABRICATION

CROSS-REFERENCE TO RELATED APPLICATIONS

This application claims the benefit of U.S. Provisional Application No. 61/162,596, filed Mar. 23, 2009, which is incorporated herein by reference.

TECHNICAL FIELD

The present application relates to an epidural stimulation lead, and in particular, to an epidural stimulation lead adapted for percutaneous insertion.

BACKGROUND

Application of specific electrical fields to spinal nerve roots, spinal cord, and other nerve bundles for the purpose of chronic pain control has been actively practiced since the 1960s. While a precise understanding of the interaction between the applied electrical energy and the nervous tissue is not fully appreciated, it is known that application of an electrical field (or stimulation) to spinal nervous tissue (i.e., spinal nerve roots and spinal cord bundles) can effectively mask certain types of pain transmitted from regions of the body associated with the stimulated tissue. More specifically, applying particularized electrical energy to the spinal cord associated with regions of the body afflicted with chronic pain can induce paresthesia, or a subjective sensation of numbness or tingling, in the afflicted bodily regions. This paresthesia can effectively mask the transmission of non-acute pain sensations to the brain.

Successful pain management and the avoidance of stimulation in unafflicted regions necessarily require that the applied electric field or stimulation be properly positioned longitudinally along the dorsal column. Positioning of an applied electrical field relative to a physiological midline is also important.

Nerve fibers relating to certain peripheral areas extend between the brain and a nerve root along the same relative side of the dorsal column as the corresponding peripheral areas. Pain that is concentrated on only one side of the body is "unilateral" in nature. In contrast, pain that is present on both sides of a patient is "bilateral." To address unilateral pain, electrical energy may be applied to neural structures on the side of a dorsal column that directly corresponds to a side of the body subject to pain. Accordingly, bilateral pain is typically treated through either an application of electrical energy along a patient's physiological midline or an application of electrical energy that transverses the physiological midline.

The applied electric field is commonly delivered through electrodes positioned external to the dura layer surrounding the spinal cord. The electrodes are typically carried by two primary vehicles: percutaneous leads and laminotomy leads.

Percutaneous leads commonly have a circular cross-section (typically in the range of 0.05 inches) and three or more, equally-spaced ring electrodes. Percutaneous leads are typically placed above the dura layer of a patient using a Touhy-like needle. For insertion, the Touhy-like needle is passed through the skin, between desired vertebrae, to open above the dura layer. For unilateral pain, percutaneous leads are positioned on a side of a dorsal column corresponding to the "afflicted" side of the body, as discussed above, and for bilateral pain, a single percutaneous lead is positioned along the patient midline (or two or more leads are positioned on each side of the midline). Because of their relatively small dimensions, percutaneous leads typically are implanted with a less-invasive method than used for laminotomy leads. Furthermore, a user has the ability to create a large variety of electrode array patterns by using a plurality of leads.

In contrast, laminotomy leads have a paddle configuration and typically possess a plurality of electrodes (for example, two, four, eight, or sixteen) arranged in one or more columns. The exposed surface area of the plurality of electrodes is commonly confined to only one surface of the laminotomy lead, thus facilitating a more focused application of electrical energy.

Laminotomy leads are typically implanted transversely centered over the physiological midline of a patient. In such position, multiple columns of electrodes are well suited to address both unilateral and bilateral pain, where electrical energy may be administered using either column independently (on either side of the midline) or administered using both columns to create an electric field which traverses the midline.

A multi-column laminotomy lead usually enables reliable positioning of a plurality of electrodes, and in particular, a plurality of electrode columns that do not readily deviate from an initial implantation position. Furthermore, they are capable of being sutured in place. So, there is less migration in the operating environment of the human body. Thus, they typically offer greater stability than percutaneous leads.

Given the relative larger dimensions of conventional laminotomy leads, a surgical procedure is usually required for implantation. The surgical procedure, or partial laminectomy, requires the resection and removal of certain vertebral tissue and often a portion of the vertebra to allow both access to the dura and proper positioning of a laminotomy lead.

When selecting whether to use percutaneous leads or a laminotomy lead, therefore, the surgeon balances the risks of a more invasive surgical procedure against the advantages of using a laminotomy lead.

SUMMARY

In one embodiment, a paddle-style lead for implantation in the epidural space through an insertion tool, the paddle-style lead comprising: a lead body; a plurality of conductors extending from a proximal portion of the lead body to a distal portion of the lead body; a plurality of terminals that are electrically coupled to the plurality of terminals; and a paddle structure that comprises a frame of rigid material, the frame comprising first, second, and third longitudinal members, a distal linking portion that is mechanically coupled to the first, second, and third longitudinal members, and a proximal linking portion that is mechanically coupled to the first, second, and third longitudinal members; wherein a respective plurality of electrodes are provided for each of the first, second, and third longitudinal members, each plurality of electrodes being electrically coupled to conductors of the plurality of conductors; wherein the distal and proximal linking portions are adapted to permit compression of the first and third longitudinal members toward each other and to permit the second longitudinal member to move out of plane relative to the first and third longitudinal members when a compressive force is applied to the paddle.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

FIG. 1c is a detailed view of an electrode of the lead shown in FIG. 1a.

FIG. 7a is an isometric view of a laminotomy lead kit according to another inventive embodiment.

FIG. 7b is a detailed isometric view of a distal portion of laminotomy lead kit of FIG. 7a.

FIG. 8a is a plan view of a proximal end of a lead.

FIG. 8b depicts an implantable pulse generator coupled to a laminotomy lead according to one inventive embodiment.

DETAILED DESCRIPTION

Some representative embodiments are directed to flexible paddle stimulation leads for percutaneous implantation wherein the flexible paddle stimulation leads have a distal end portion which is capable of expanding from an insertion configuration to an implantation configuration. There are also disclosed various methods of inserting a flexible paddle stimulation lead into a body, the methods include percutaneously positioning a tubular member adjacent to a site to receive therapeutic stimulation, compressing a lateral dimension of a distal end portion of an implantable lead, inserting the distal end portion into a tubular member, urging the distal end portion through the tubular member, expanding the lateral dimension of the distal end portion such that the distal end portion is placed to deliver therapeutic stimulation. In certain embodiments, there may be a system comprising a flexible paddle stimulation lead and insertion tools for percutaneously implanting the flexible paddle portion adjacent to a stimulation site.

Figure 1A:
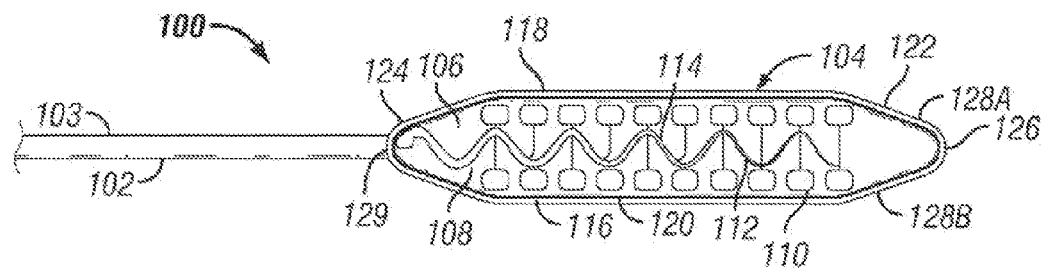
FIG. 1a is a top view of a laminotomy lead according to one inventive embodiment.

FIG. 1a is a plan view of a flexible paddle 100 of a laminotomy lead 102. The lead 102 is adapted for implantation into the epidural space of a patient for stimulation of fibers of the dorsal column of a patient's spinal cord. Lead 102 could alternatively be employed for any other tissue stimulation application. The lead 102 comprises a lead body 103 having a proximal end (not shown) and a distal end portion, such as the flexible paddle 100. The lead body 103 comprises a plurality of conductors (not shown) embedded or otherwise contained within insulative material.

The flexible paddle 100 comprises a longitudinal frame 104 and elastic membrane 106 disposed across the interior surface area defined by frame 104. The elastic membrane 106 has a first side or face 108 and a second side (not shown). A plurality of electrodes 110 are positioned on the first face 108 of the elastic membrane 106. A plurality of conducting elements 112 are disposed on the paddle to electrically couple the plurality of electrodes 110 to conductors (not shown) contained or embedded within the insulative material of lead body 103. The conductors are connected to terminals (not shown) positioned at the proximal end of the lead body 103.

Paddle 100 is adapted to deform to permit paddle 100 to be inserted through the lumen of a needle or suitable insertion tool into the epidural space of a patient. Such deformation permits paddle 100 to be implanted within the epidural space of a patient without requiring a partial laminectomy. After paddle 100 reaches the distal end of the needle or insertion tool, paddle 100 is adapted to resume its original shape thereby permitting the electrodes 110 to be positioned in an advantageous manner for spinal cord stimulation. As illustrated in FIG. 1a, the flexible paddle 100 is shown in its fully expanded or relaxed state.

Figure 1B:
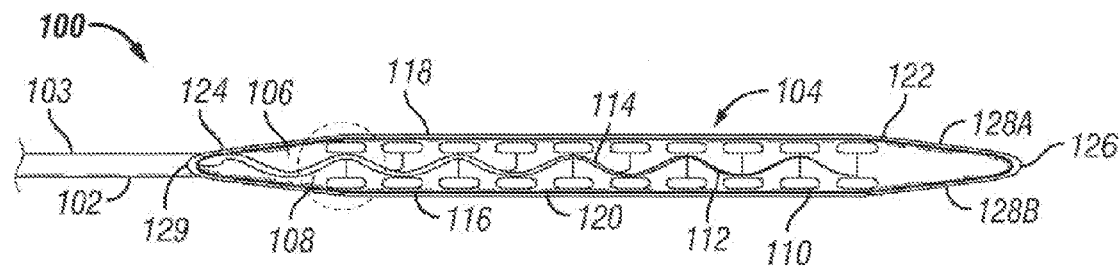
FIG. 1b is a top view of the laminotomy lead of FIG. 1a in a second or insertion configuration.

FIG. 1b is a plan view of the flexible paddle 100 in an elongated or insertion configuration.

Frame 104 of paddle 100 is adapted for such deformation by including a first longitudinal portion 118, a second longitudinal portion 120, a distal biasing or spring member 122 and a proximal spring member 124. As illustrated, the distal spring member 122 may be shaped similar to a "V" having the rounded tip portion 126 and two arms 128a and 128b. The proximal spring member 124 may also be shaped in a V, but with a different orientation. A tip portion 129 of the proximal spring member 124 points toward the proximal direction. In certain embodiments, frame 104 is formed using a rigid or high durometer, biocompatible, biostable polymer. As used herein, the term "rigid" refers to the degree of deformability of frame. That is, frame 104 tends to change its configuration without undergoing appreciable deformation. In contrast, membrane 106 deforms or stretches when paddle 100 changes states. Examples of suitable polymers for frame 104 include polyimide, polyetheretherketone (PEEK), polyetherketone ketone (PEKK), and liquid crystal polymer (LCP). In some alternative embodiments, all of the frame 104 or selected portions thereof (e.g., spring members 122 and 124) may be made from or include metallic material.

In the fully relaxed state, springs 122 and 124 maintain longitudinal portions 118 and 120 at a distance apart as shown in FIG. 1a. In one embodiment, during an implantation procedure, paddle 100 is inserted into the lumen of an insertion tool and spring 122 contacts the inner surface of the tool defined by the lumen. The contact force tends to "pinch" the spring member thereby providing a compressive force to the spring member. The compression of spring 122, in turn, brings longitudinal portions 118 and 120 closer together as shown in FIG. 1b. Spring 124 is also compressed due to its mechanical coupling to members 118 and 120.

The elastic membrane 106 is preferably fabricated from a low durometer and elastic biocompatible material, such as CARBOSIL® (a silicone urethane copolymer) or another elastomer. The elastic nature of membrane 106 permits membrane 106 to stretch when force is applied to or removed from paddle thereby causing paddle 100 to change shapes. Paddle 100 is preferably adapted such that elastic membrane 106 is stretched longitudinally when paddle 100 is in the state shown in FIG. 1b. Alternatively, paddle 100 may be adapted such that elastic membrane 106 is stretched in latitudinal manner when paddle 100 is in the state shown in FIG. 1a.

Electrodes 110 and conducting elements 112 are preferably fabricated by depositing or otherwise providing conductive material on the elastomer material. In one embodiment, the conductive traces are built upon on a 0.001" or 0.002" film of LCP. The LCP is also adhered to a substrate using a temporary adhesive. Selected portions of the LCP film are cut away and removed leaving behind on LCP material where the body of the traces and electrodes are disposed. The remaining LCP material with traces and electrodes is laminated or coated with the appropriate elastomer. The electrodes are then exposed using a TEA laser.

In another embodiment, the conductive traces are produced directly on the elastomer by using ink jet technology or by using conventional photolithographic methods but applying them to an elastomer substrate in a stretched state. Once the metallization is complete along with plate-up the elastomer substrate is allowed to return to its natural dimensions resulting in conductive compression. In this embodiment, it is preferred to obtain superior metal to polymer adhesion.

Stretching of membrane 106 is problematic for conventional medical device fabrication techniques. Specifically, metallic material deposited or otherwise applied to known biocompatible elastomers may tend to delaminate or otherwise separate from such material when the elastic material is stretched. Electrodes 110 and conducting elements 112 are preferably implemented to substantially prevent or eliminate such separation from occurring by adapting electrodes 110 and conducting elements 112 to stretch in a corresponding manner to stretching of elastomer 106.

In certain embodiments, the conducting elements 112 are disposed on the paddle surface in a manner that elements 112 comprise a plurality of curves which allow the conducting elements 112 to "stretch" as paddle 100 changes states between the states shown in FIGS. 1a and 1b. Each conducting element 112 is formed using a continuous trace of metallic material applied to membrane 106. In a preferred embodiment, the continuous trace repetitively curves or winds in alternative directions in a serpentine manner. The alternating shape of the respective metal traces permits conducting elements 112 to elongate as the frame 104 and membrane 106 changes states. The width of the curves of the continuous trace may be uniform or may vary along the length of paddle 100.

Figure 1C:
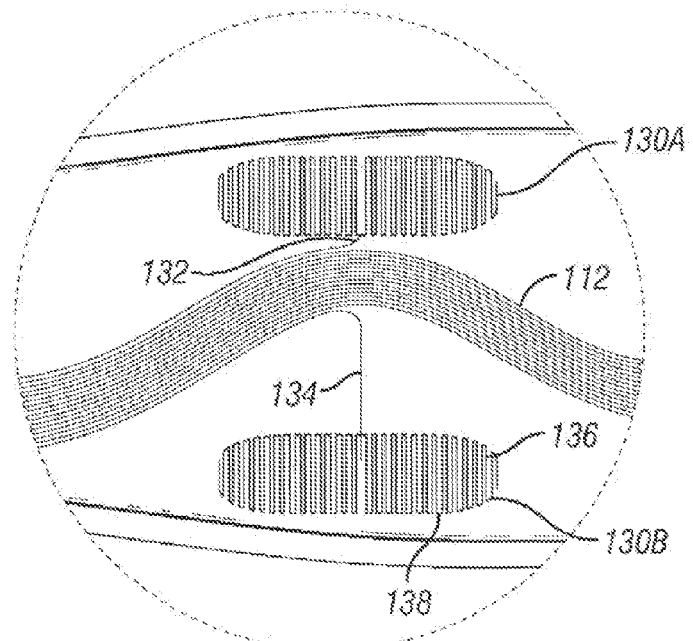

Electrodes 110 are also preferably fabricated to substantially prevent separation of electrodes 110 from elastic membrane 106. FIG. 1c is a detail view of one embodiment of two electrodes 130a and 130b which are members of the plurality of electrodes 110 (FIGS. 1a and 1b). Electrodes 130a and 130b are formed using a continuous trace of metallic material applied to membrane 106. The continuous trace repetitively curves or winds in alternative directions in a serpentine manner. The alternating shape of the respective metal traces permits electrodes 130a and 130b to elongate as the frame 104 changes states. The width of the curves of the continuous trace may be uniform along the length of electrodes 130a or may vary as desired to effect the charge transfer characteristics of the electrodes. Two lateral portions 132 and 134 of two conducting elements are illustrated branching off from the curved portions of the conducting elements 112.

In some embodiments, when paddle 100 is to be implanted, the frame 104 and the elastic membrane 106 may be elongated with a stylet to assume an insertion configuration as illustrated in FIG. 1b. As the longitudinal body is elongated, the lateral profile of the frame 104 decreases which allows the longitudinal body to be inserted into an appropriate insertion tool (not shown). When the frame 104 exits the insertion tool and the stylet no longer elongates the frame 104, the spring members 122 and 124 are no longer subject to the compressive forces and can expand to a predetermined distance as illustrated in FIG. 1a. The electrodes 110 may then be positioned within the epidural space in a manner that is similar to an electrode spacing of a conventional paddle-style lead.

Paddle 100 may be placed within the epidural space of a patient using any suitable epidural needle or other insertion tool. Examples of surgical implantation and insertion tools that can be utilized with paddle 100 are described in U.S. Patent Application Publication No. 20050288759, entitled "Method and Apparatus for Implanting an Electrical Stimulation Lead Using a Flexible Introducer," and U.S. Patent Application Publication No. 20050209667, entitled "Stimulation Sensing Lead Adapted for Percutaneous Insertion," both disclosures are herein incorporated by reference. Additionally, an expandable paddle may be introduced through a suitable tool while the paddle is held within a tube structure according to one representative embodiment. The tube structure may be fabricated from a suitable polymer material. The wall thickness of the tube structure may preferably be relatively small (e.g., a few thousands of an inch). An embedded monofilament or fine wire may be included within the wall to provide additional strength or rigidity to the tube structure. During introduction, the expandable paddle structure is maintained in a compressed state by the wall of the tube structure. The surgeon may advance and steer the tube structure within the epidural space. Upon reaching the appropriate implant position, the surgeon may withdraw the tube structure while leaving the paddle in place. At this point, the paddle would expand due to its structural characteristics. Such a tube structure may also facilitate explantation of a paddle structure if a surgeon deems removal of a previously implanted paddle as medically appropriate. In an alternative embodiment, the tubular structure may be integrated with the lead body. In this embodiment, the tubular structure may be retracted to expose the paddle thereby permitting the paddle to expand. Likewise, upon explantation, the tubular structure may be advanced to collapse the paddle.

Figure 2:
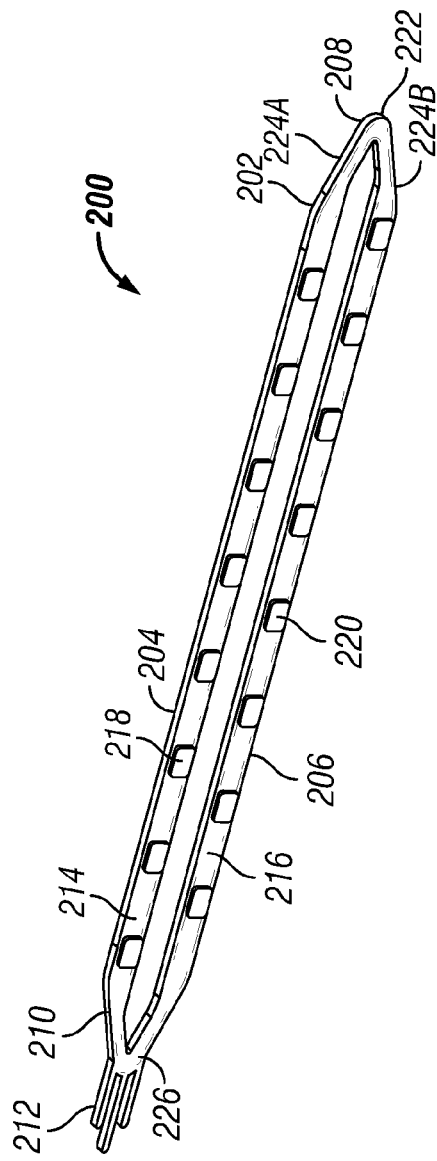
FIG. 2 is an isometric view of a laminotomy lead according to another inventive embodiment.

FIG. 2 is an isometric view of flexible paddle 200 for use with a laminotomy lead. The flexible paddle 200 comprises a frame 202 which may be formed from a high durometer, biocompatible, biostable polymer, such as PEEK or PEKK. As illustrated, the frame 202 comprises a first longitudinal member 204, a second longitudinal member 206, a distal spring member 208, and a proximal spring member 210. In certain embodiments, the proximal spring 210 may be coupled to a laminotomy lead connector 212. In certain embodiments, the laminotomy lead connector 212 couples to a female lamitrode connector (not shown) positioned on the distal portion of a lead (not shown), although any suitable electrical connections could be employed. When the laminotomy lead connector 212 is coupled to the corresponding female laminotomy lead connector, an electrical connection is possible between conductors in a lead body and conducting elements within the flexible paddle 200.

The first longitudinal member 204 and the second longitudinal member 206 each have a first side or face 214, 216, respectively and a second side or face (not shown). In certain embodiments, a first plurality of electrodes 218 may be positioned on the first face 214 of the first longitudinal member 204. Similarly, a second plurality of electrodes 220 may be positioned on the first face 214 second face 216 of the second longitudinal member 206.

In some embodiments, electrodes 218 and 220 are formed using an ink-jetting process using commercially available ink-jetting techology. The ink comprises gold particles that range from 2-10 nanometers in a solvent carrier with a small amount of lignan. When heated to 170° C., the organics evaporate thereby leaving the nano gold particles to fuse to each other. To facilitate bonding of the gold particles to the PEEK substrate, a single mono-molecular layer of mercaptotrimethoxysilane or similar compound is employed. The mercapto or thio groups bond to gold on one side of the molecule while the silane portion of the molecule bonds to the PEEK surface (optionally modified by an oxygen plasma) on the other side of the molecule. The jetted conductive pattern (s) are then plated with suitable biocompatible materials, such as gold, platinum, platinum iridium, etc. using conventional electro-plating processes.

A plurality of conducting elements (not shown) electrically couple the first and second plurality of electrodes 218 and 220 to the laminotomy lead connection 212. The conducting elements may be deposited or otherwise applied between respective layers of insulative material of frame 202. In other embodiments, the conducting elements may be traces disposed on the second face of members 204 and 206 and covered by a thin layer of insulative material. Vias may be employed during paddle fabrication to permit electrical coupling between the conducting elements and electrodes 218 and 220.

In an alternative embodiment, electrodes 218 and 220 and suitable electrical conducting elements may be formed on one or more layers of flex film laminated or otherwise attached to frame 202.

In certain embodiments, a thin layer of elastic material may be provided between the first longitudinal member 204 and the second longitudinal member 206 to prevent fibrous growth of tissue between the longitudinal members after the paddle 200 has been implanted.

In certain embodiments, the distal spring member 208 may be shaped so that when the tip portion 222 of the spring member encounters an inner wall of a tubular insertion tool (not shown), the contact force tends to "pinch" the spring member thereby providing a compressive force to the spring member. As illustrated, the spring member 208 may be shaped similar to a "V" having a rounded tip portion 222 and two arms 224a and 224b.

In certain embodiments, the proximal spring member 210 may also be shaped into a "V" shape having a vertex or tip portion 226. In certain embodiments, the tip portion 226 of the proximal spring member 210 points toward the proximal direction. This allows the proximal spring member 210 to collapse in situations where explantation of the paddle is necessary.

Thus, when the flexible paddle 200 is to be implanted, the distal spring member 208 can be inserted into a tubular insertion tool (not shown). The insertion of the spring member 208 will pinch the arms 224a and 224b as they enter the tubular insertion tool. The pinching will place a compressive force on the arms 224a and 224b, which will cause the members to move towards each other. In turn, the longitudinal members 204 and 206 will laterally compress towards each other. This compression reduces the lateral profile of the flexible paddle 200 which allows the flexible paddle 200 to be inserted into an appropriate implantation tool. When the flexible paddle 200 exits the implantation tool, the spring members 208 and 210 are no longer subject to the compressive forces imposed by the tubular insertion tool and can expand apart. The electrodes 218 and 220 may then be positioned within the epidural space in a manner that is similar to an electrode spacing of a conventional paddle-style lead.

Figure 3:
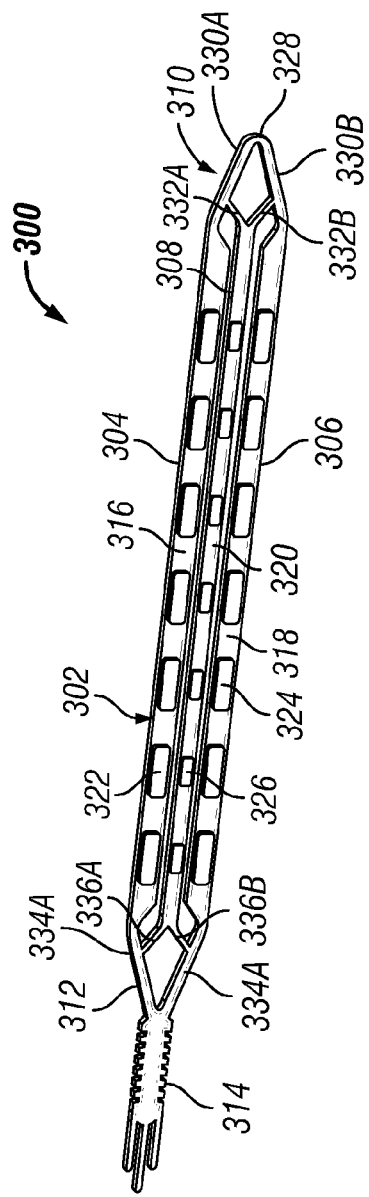
FIG. 3 is an isometric view of a laminotomy lead according to another inventive embodiment.

FIG. 3 is an isometric view of another embodiment of a flexible paddle 300 of a distal end of a laminotomy lead according to one inventive embodiment. The flexible paddle 300 may comprise a frame 302 which may be formed from a high durometer, biocompatible, biostable polymer, such as PEEK, PEKK, or LCP.

As illustrated, the frame 302 comprises a first longitudinal Member 304, a second longitudinal member 306, a middle longitudinal member 308, a distal spring member 310, and a proximal spring member 312. In certain embodiments, the proximal spring member 312 may be coupled to a laminotomy lead connector 314. In certain embodiments, the laminotomy lead connector 314 couples to a female lamitrode connector (not shown) positioned on the distal portion of a lead body (not shown), although any suitable electrical connections could be employed.

The first longitudinal member 304, the second longitudinal member 306, and the middle longitudinal member 308 each have a first side or face 316, 318, and 320 respectively and a second side or face (not shown). In certain embodiments, a first plurality of electrodes 322 may be positioned on the first face 316 of the first longitudinal member 304. Similarly, a second plurality of electrodes 324 may be positioned on the first face 318 of the second longitudinal member 306 and a third plurality of electrodes 326 may be positioned on the first face 320 of the middle longitudinal member 308. The electrodes of the first, second, and third plurality of electrodes 322, 324, and 326 may be formed in an suitable manner including the process described above in regard to paddle 200 of FIG. 2.

A plurality of conducting elements (not shown) electrically couple the first, second, and third plurality of electrodes 322, 324, 326 and to the laminotomy lead connector 314. In certain embodiments, the conducting elements may be provided within the insulative material of the respective longitudinal member 304, 306 and 308. In other embodiments, the conducting elements may be traces deposited or otherwise provided on the second face of longitudinal member 304, 306, and/or 308.

In other embodiments, a flex-circuit may be employed to provide electrodes and the conducting elements where the flex-circuit is attached or laminated to the PEEK, PEKK, or LCP material of frame 302.

In certain embodiments, a thin elastic layer may be positioned between the longitudinal members to prevent a fibrous growth of tissue between the longitudinal members of the flexible paddle 300 after the flexible paddle 300 has been implanted.

In certain embodiments, the distal spring member 310 may be shaped so that when a tip portion 328 of the spring member encounters an inner wall of a tubular insertion tool (not shown), the contact force tends to "pinch" the spring member thereby providing a compressive force to the spring member. As illustrated, the distal spring member 310 may be shaped similar to a "V" having a rounded tip portion 328 and two arms 330a and 330b. In certain embodiments, two linkage members 332a and 332b couple the middle longitudinal member 308 to the distal spring member 310. In some embodiments, there may be a detent formed at the intersection of the linkage members 332a-332b and the spring arms 330a-330b. The detent biases the linkage members to deflect in a predetermined direction when the spring arms 330a-330b are compressed.

In certain embodiments, the proximal spring member 312 may also comprise arm members 334a-334b which are coupled together to form a "V" shape. In some embodiments, the vertex of the V shape of the proximal spring member 312 points toward the proximal direction. This allows the proximal spring member 312 to collapse in situations where explantation of the paddle is necessary. In certain embodiments, two linkage members 336a and 336b couple the middle longitudinal member 308 to the proximal spring member 312. In some embodiments, there may be a detent formed at the intersection of the linkage members 336a-336b and the spring arms 332a-332b. The detent biases the linkage members to deflect in a predetermined direction when the spring arms 334a-334b are compressed.

When the flexible paddle 300 is implanted, the distal spring member 310 can be inserted into a tubular insertion tool (not shown). The insertion of the spring member 312 will pinch the arms 330a and 330b together as they enter the tubular insertion tool. The pinching will place a compressive force of the arms 330a and 330b, which will cause the members to deflect towards each other. As the arms 330a and 330b begin to move, the linkage members 332a and 332b deflect out of the plane formed by the first longitudinal member 304 and the second longitudinal member 306. The middle longitudinal member 308 is also carried out of its position or plane by the movement of the linkage members 332a and 332b. At the proximal end, the linkage members 336a-336b also allow the middle longitudinal member 308 to move out of plane. Once the middle longitudinal member is out of the plane, the longitudinal members 304 and 306 are free to laterally compress towards each other. This compression reduces the lateral width of the flexible paddle 300 which allows the flexible paddle 300 to continue to be inserted through the tubular insertion tool. Although three longitudinal members are shown for paddle 300, paddles having a greater number of longitudinal members can be implemented to allow the respective members to collapse together with certain longitudinal members moving out of plane.

When the flexible paddle 300 exits the implantation tool, the spring members 310 and 312 are no longer subject to the compressive forces of the tubular insertion tool and can expand to a predetermined distance. The expansion of the spring members allows the longitudinal members 304-306 to follow and also expand while at the same time moving the middle longitudinal member 308 back into its original plane. The plurality of electrodes 322, 324, 326 may then be positioned within the epidural space in a manner that is similar to an electrode spacing of a conventional paddle-style lead.

Figure 4:
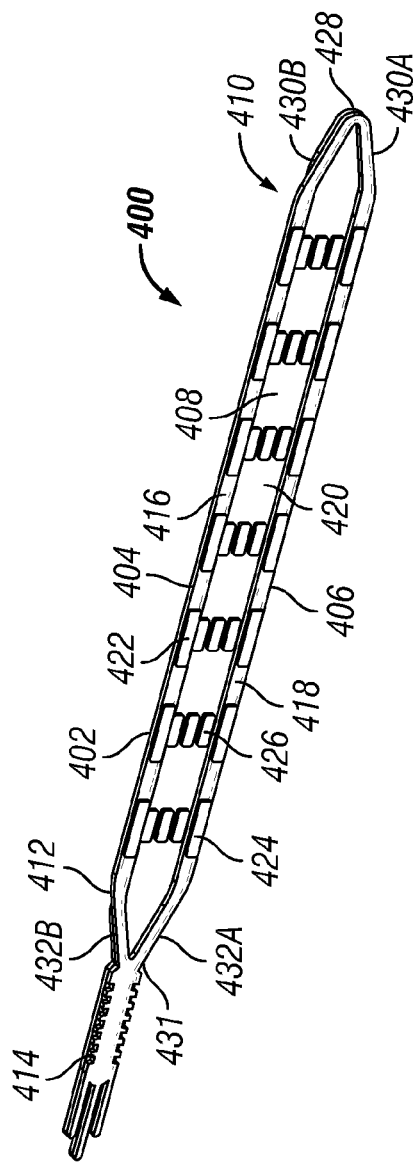
FIG. 4 is an isometric view of a laminotomy lead according to another inventive embodiment.

FIG. 4 is an isometric view of another inventive flexible paddle 400 for a distal end of a laminotomy lead. The flexible paddle portion 400 may comprise a frame 402 which may be formed from a high durometer, biocompatible, biostable polymer, such as PEEK or PEKK.

As illustrated, the frame 402 comprises a first longitudinal member 404, a second longitudinal member 406, a middle longitudinal member 408, a distal spring member 410, and a proximal spring member 412. In certain embodiments, the proximal spring member 412 may be coupled to a laminotomy lead connector 414. In certain embodiments, the laminotomy lead connector 414 couples to a female lamitrode connector (not shown) positioned on the distal portion of a lead body (not shown), although any suitable electrical connections could be employed.

The first longitudinal member 404, the second longitudinal member 406, and the middle longitudinal member 408 each have a first side or face 416, 418, and 420 respectively and a second side or face (not shown). In certain embodiments, a first plurality of electrodes 422 may be positioned on the first face 416 of the first longitudinal member 404. Similarly, a second plurality of electrodes 424 may be positioned on the first face 418 of the second longitudinal member 406 and a third plurality of electrodes 426 may be positioned on the first face 420 of the middle longitudinal member 408. In the illustrative embodiment, the third plurality of electrodes 426 comprises three columns of electrodes. In other embodiments, there may only be one or two columns of electrodes. The electrodes of the first, second, and third plurality of electrodes may be formed using any suitable process including the deposition process discussed in regard to paddle 200 of FIG. 2.

A plurality of conducting elements (not shown) electrically couple the first, second, and third plurality of electrodes 422, 424, 426 and to the laminotomy lead connection 414. In certain embodiments, the conducting elements may be formed within layers of the insulative material of longitudinal member 404, 406 and 408. In other embodiments, the conducting elements may be traces provided on the second respective faces of longitudinal member 404, 406, and/or 408.

In certain embodiments, the distal spring member 410 may be shaped so that when the spring member encounters an inner wall of a tubular insertion tool (not shown), the contact force tends to "pinch" the spring member thereby providing a compressive force to the spring member. As illustrated, the spring member 410 may be shaped similar to a "V" having a vertex or rounded tip portion 428 and two arms 430a and 430b.

In certain embodiments, the proximal spring member 412 may also comprise arm members 432a-432b which are coupled together to form a "V" shape. In some embodiments, a vertex 431 of the V shape of the proximal spring member 412 points toward the proximal direction. This allows the proximal spring member 412 to collapse in situations where explantation is necessary.

In certain embodiments, the middle longitudinal member 408 is coupled to the distal spring member 410 close to the tip portion 428. The middle longitudinal member 408 may also be coupled to the proximal spring member 412 close to the vertex 431 of the proximal spring member 412. Coupling the middle longitudinal member 408 to the spring members close to their respective vertexes allows the spring arms to move freely with respect to the middle longitudinal member. In turn, the first longitudinal member 404 and the second longitudinal member 406 are also free to move with respect to the middle longitudinal member 408.

When the flexible paddle 400 is implanted, the distal spring member 410 can be inserted into a tubular insertion tool (not shown). The insertion of the distal spring member 410 will pinch its arm members 430a and 430b together as they enter the tubular insertion tool. The pinching will place a compressive force on the arm members 430a and 430b, which will cause the arm members to deflect towards each other. The movement of arm members 430a and 430b will cause the longitudinal members 404 and 406 to follow and laterally compress towards each other. The middle longitudinal member 408 is in a different plane than the springs 410, 412 and the longitudinal members 404 and 406. This positioning allows the longitudinal members 404 and 406 to compress with respect to each other without interference from the middle longitudinal member 408. This compression reduces the lateral width of the flexible paddle 400 which allows the flexible paddle 400 to be inserted through an appropriate implantation tool.

When the flexible paddle 400 exits the implantation tool, the spring members 408 and 410 are no longer subject to the compressive forces of the tubular insertion tool and can expand to a predetermined distance. Similarly the longitudinal members 404 and 406 follow and also expand relative to each other. The electrodes 418 may then be positioned within the epidural space in a manner that is similar to an electrode spacing of a conventional paddle-style lead.

Figure 5A:
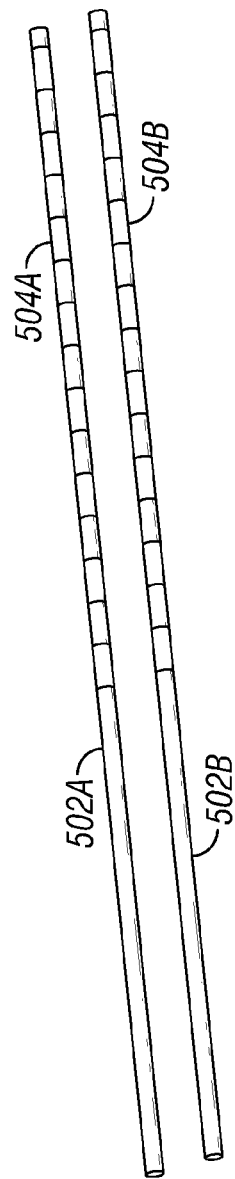
FIG. 5a is an isometric view of two percutaneous leads which could be incorporated into the laminotomy lead kits of FIGS. 5b-5d, FIG. 6, and FIG. 7.

According to other alternative inventive embodiments, a conversion kit may be provided to stably position percutaneous leads within the epidural space in a manner that may have some of the benefits and characteristics of flexible laminotomy leads. FIG. 5a illustrates the distal end portion of two percutaneous stimulation leads 502a and 502b each having a plurality of stimulation electrodes 504a and 504b which are coupled to conductors (not shown) running longitudinally within the leads 502a and 502b. For purposes of illustration only, the leads 502a and 502b are shown with eight stimulation electrodes in each plurality of stimulation electrodes 504a-504b. As will be appreciated by those skilled in the art, any number of stimulation electrodes may be utilized as desired within the leads 502a and 502b. In this illustrative embodiment, the pluralities of stimulation electrodes 504a and 504b are shown as band or ring electrodes. In certain embodiments, the stimulation electrodes 504a and 504b may be formed of biocompatible, conductive materials which do not develop a significant amount of oxide films, such as platinum and platinum-iridium, or other conductive materials, metals or alloys known to those skilled in the art. An example of a suitable commercially available lead which could be used as stimulation leads 502a-502b is the Axxess® lead available form St. Jude Medical Neuromodulation Division (Plano, Tex.).

Figure 5B:
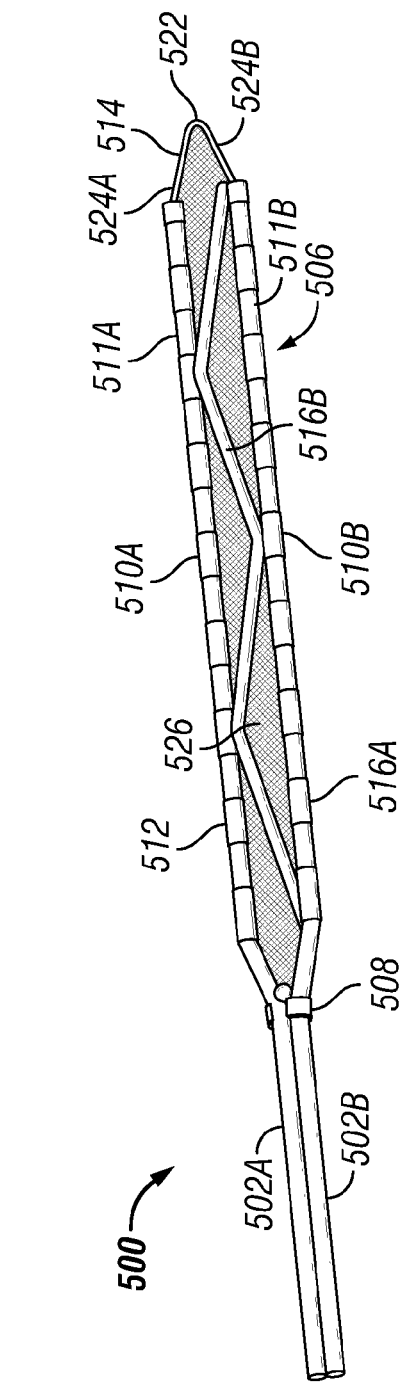
FIG. 5b is an isometric view of a laminotomy lead kit according to one inventive embodiment.

Turning now to FIG. 5b, there is one embodiment of an assembly or kit 500 using the stimulation leads 502a and 502b. The assembly 500 may comprise a frame 506 and a retention clip 508 to retain the stimulation leads 502a-502b together. The retention clip 508 may also facilitate the removal of the assembly 500 from the epidural space if the leads 502a-502b need to be explanted.

The frame 506 may comprise two longitudinal members 510a and 510b. In certain embodiments, the longitudinal members 510a-510b may be tubular members fabricated from a relatively high durometer, biocompatible, biostable polymer. Examples of suitable polymers include PEEK, PEKK, and LCP. In certain embodiments, the tubular members may have internal diameters which are sized to accommodate the external diameters of the stimulation leads 502a-502b such that the longitudinal members 510a-510b can slide over the stimulation leads 502a and 502b, respectively. In certain embodiments, there may be a series of openings or apertures 511a-511b which are configured to align with the stimulation electrodes 504a-504b of the stimulation leads 502a-502b. The apertures 511a-511b may be formed from ablating portions of the walls of the longitudinal members 510a-510b with a suitable laser. When suitably assembled and aligned, the apertures 511a-511b may cause the field under the corresponding electrodes to be substantially unidirectional.

Figure 5C:
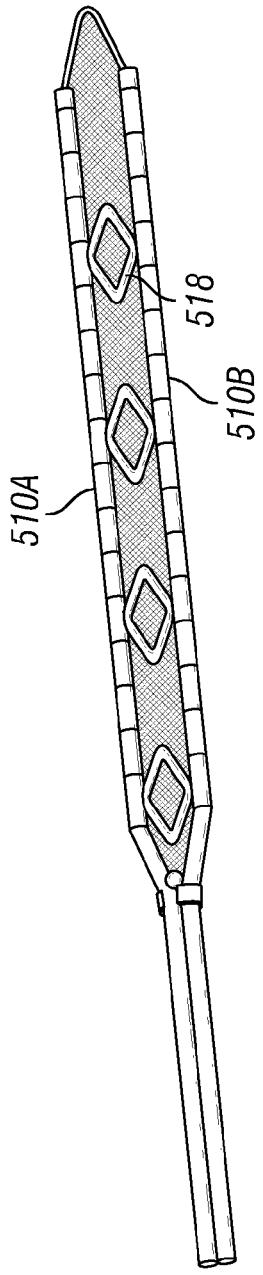
FIG. 5c is an isometric view of a laminotomy lead kit according to another inventive embodiment.
Figure 5D:
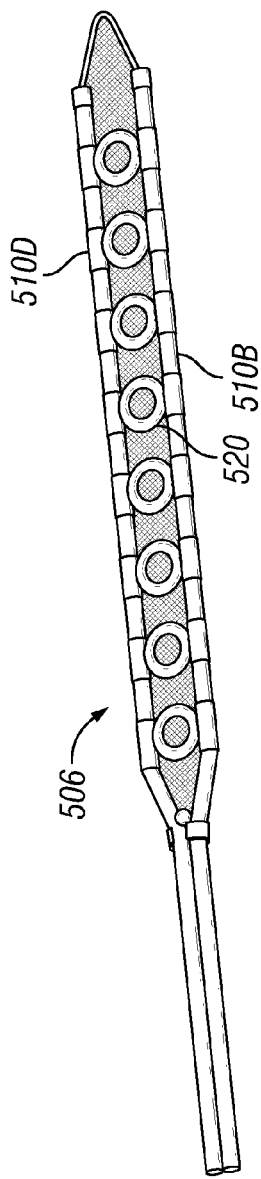
FIG. 5d is an isometric view of a laminotomy lead kit according to another inventive embodiment.

In certain embodiments, a primary spring or springs 512 couples to the longitudinal members 510a-510b and maintains the longitudinal members in a substantially parallel arrangement. In certain embodiments, there may also be a distal end spring member 514, which may be configured to assist in the percutaneous placement of assembly 500. In the embodiment illustrated by FIG. 5b, the primary spring 512 is a pair of leaf springs 516a-516b which act to bias the arms at a predetermined distance apart. Other types of biasing may also be used for the primary spring 512. As an example, in FIG. 5c, there is illustrated an embodiment where a series of diamond springs 518 which bias the longitudinal members 510a-510b at a predetermined distance. FIG. 5d illustrates another example where the primary springs 512 of the frame 506 are a series of O-rings 520 are used as biasing members to maintain the longitudinal members 510a and 510b at a predetermined distance.

Turning back to FIG. 5b, it can be seen that in certain embodiments, the distal spring member 514 may be shaped so that when the tip portion 522 of the distal spring member encounters an inner wall of a tubular insertion tool (not shown), the contact force tends to "pinch" the spring member thereby providing a compressive force to the spring member. As illustrated, the distal spring member 514 may be shaped similar to a "V" having a rounded tip portion 522 and two arms 524a and 524b which couple to the longitudinal members 510a and 510b, respectively.

The primary spring 512 and distal spring 514 may also be made out of such materials possessing a spring memory characteristic, such as PEEK or a suitable biocompatible metal. In some alternative embodiments, the primary spring 512 and the distal spring 514 may be made from metal spring elements or a combination of PEEK and metal elements. For instance, in certain embodiments, the longitudinal members 510a and 510b of the frame 506 and the primary spring 512 may be made from PEEK and the distal spring 514 may be made from a biocompatible metal.

In certain embodiments, a thin elastic layer 526 may be positioned between the first longitudinal member 510a and the second longitudinal member 510b to prevent a fibrous growth of tissue between the longitudinal members after the assembly 500 has been implanted.

When the assembly 500 is to be implanted, the distal spring member 514 can be inserted into a tubular insertion tool (not shown). The insertion of the spring member 514 will pinch the arm members 524a and 524b as they enter the tubular insertion tool. The pinching will place a compressive force on the arm members 524a and 524b, which will cause the members to move towards each other. In turn, the longitudinal members 510a and 510b will follow the movement of the arm members 524a-524b and laterally compress towards each other as the compression forces overcome the biasing force of the primary spring(s) 512. This compression reduces the lateral profile of the assembly 500 which allows the assembly to be inserted into an appropriate implantation tool. When the assembly 500 exits the implantation tool, the spring members 512 and 514 are no longer subject to the compressive forces imposed by the tubular insertion tool and can expand to a predetermined distance. The assembly 500 and the associated electrodes 504a and 504b may then positioned within the epidural space in a manner that is similar to an electrode spacing of a conventional paddle-style lead.

Figure 6:
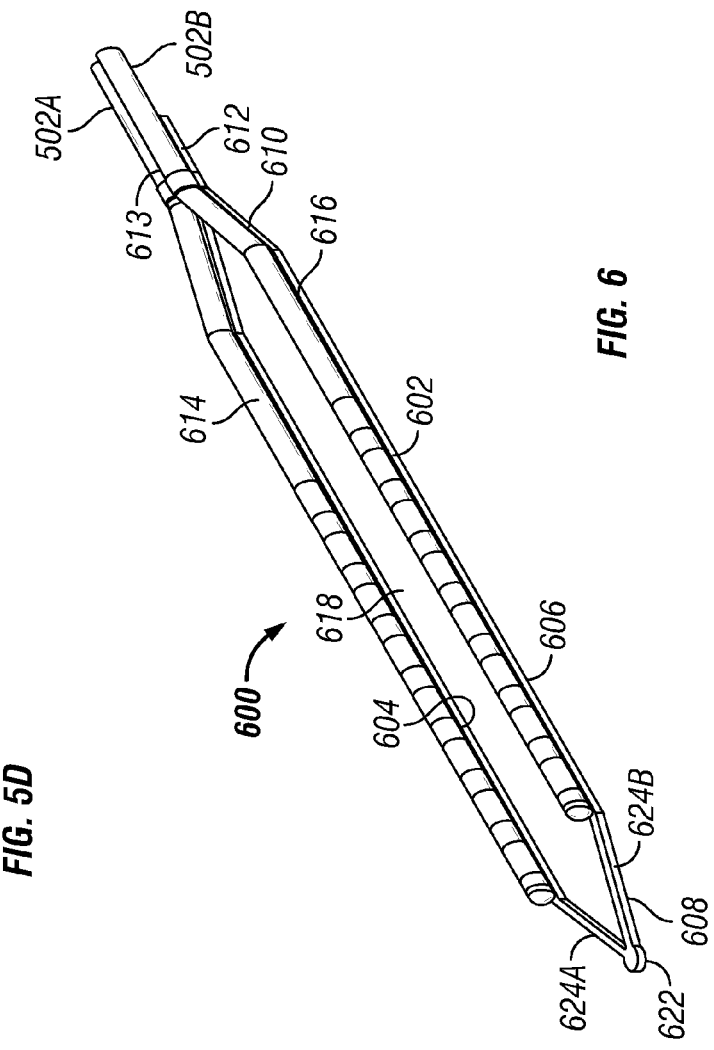
FIG. 6 is an isometric view of a laminotomy lead kit according to another inventive embodiment.

Turning now to FIG. 6, there is another embodiment of an assembly or kit 600 using the stimulation leads 502a and 502b and a frame 602. As illustrated, the frame 602 comprises a first longitudinal member 604, a second longitudinal member 606, a distal spring portion 608, and a proximal spring portion 610. In certain embodiments, the proximal spring portion 610 may be coupled to a support member 612. In certain embodiments, the support member 612 couples to the stimulation leads 502a and 502b. In one embodiment, there may be one or more retaining clips 613 to couple the support member 612 to the stimulation leads 502a-502b. In certain embodiments, the frame 602 may be formed from a high durometer, biocompatible, biostable polymer, such as PEEK, PEKK, or LCP.

The first longitudinal member 604 and the second longitudinal member 606 each have a first side or face 614, 616, respectively and a second side or face (not shown). In certain embodiments, a first plurality retaining clips (not shown) secures the leads to first face 614 of the first longitudinal member 604. Similarly, a second plurality of retaining clips (not shown) may be positioned on the first face 616 of the second longitudinal member 606 to secure the lead 502b to the longitudinal member 606.

In certain embodiments, a thin elastic layer 618 may be positioned between the first longitudinal member 604 and the second longitudinal member 606 to prevent a fibrous growth of tissue between the longitudinal members after the assembly 600 has been implanted.

In certain embodiments, the distal spring portion 608 may be shaped so that when a tip portion 622 of the distal spring portion encounters an inner wall of a tubular insertion tool (not shown), the contact force tends to "pinch" the distal spring portion thereby providing a compressive force to the distal spring portion. As illustrated, the distal spring portion 608 may be shaped similar to a "V" having a rounded tip portion 622 and two arms 624a and 624b.

In certain embodiments, the proximal spring portion 610 may also be shaped into a "V" shape. In certain embodiments, the V shape of the proximal spring portion 610 points toward the proximal direction. This allows the proximal spring portion 610 to collapse in situations where a explantation is necessary.

Thus, when the assembly 600 is to be implanted, the distal spring portion 608 can be inserted into a tubular insertion tool (not shown). The insertion of the spring portion 608 will pinch the arm members 624a and 624b as they enter the tubular insertion tool. The pinching will place a compressive force on the members 624a and 624b, which will cause the members to move towards each other. In turn, the longitudinal members 604 and 606 will follow the movement of the arm members 624a-624b and laterally compress towards each other. This compression reduces the lateral profile of the assembly 600 which allows the assembly 600 to be inserted into an appropriate implantation tool. When the assembly 600 exits the implantation tool, the spring portions 608 and 610 are no longer subject to the compressive forces imposed by the tubular insertion tool and can expand to a predetermined distance. The assembly 600 and the electrodes of the stimulation leads 502a and 502b may then positioned within the epidural space in a manner that is similar to an electrode spacing of a conventional paddle-style lead.

FIG. 7a is a perspective view of another embodiment of an assembly or kit 700 using the stimulation leads 502a and 502b. The assembly 700 may comprise a frame 702 having longitudinal channels 704a and 704b for receiving the stimulation leads 502a and 502b, respectively.

In certain embodiments, the frame 702 may be formed from a solid piece of a high durometer, biocompatible, biostable polymer, such as PEEK, PEKK, or LCP. The frame may be shaped with the longitudinal channels 704a and 704b having interior diameters which allow the stimulation leads 502a and 502b to be press fit into position. In certain embodiments, clip rings (not shown) may also be used to couple the stimulation leads 502a and 502b to the frame 702.

In certain embodiments, the frame 702 may have a corrugated cross sectional shape or another shape which will facilitate bending or rolling when the frame 702 is subjected to compressive forces. For instance, FIG. 7b is a detailed view of the end of the frame 702 showing longitudinal corrugations 706, 708, 710, and 712 defined within the frame 702 which are designed to allow the frame to compress in a predicable manner when subject to lateral compression forces.

Thus, when the assembly 700 is to be implanted, the frame 702 may be laterally compressed or folded at the corrugations 706, 708, 710, and 712. This compression reduces the lateral profile of the assembly 700 which allows the assembly 700 to be inserted into an appropriate implantation tool. When the assembly 700 exits the implantation tool, the frame 702 is no longer subject to the compressive forces imposed by the tubular insertion tool and can expand as illustrated in FIG. 7. The assembly 700 and the electrodes of the stimulation leads 502a and 502b may then be positioned within the epidural space- in a manner that is similar to an electrode spacing of a conventional paddle-style lead.

FIG. 8a is an exemplary illustration of a proximal end 802 of a lead 804 which could be used with any of the paddle ends or kits discussed above. The lead 804 may have a structure or lead body 806 which has a round or substantially round cross-section. Alternatively, the cross-section of the lead body 806 may be configured in any number of cross-sectional shapes appropriate for a specific application in which the lead will be used. Depending on the particular application, the diameter of the lead body 806 may be any suitable size.

The lead body 806 may be formed of an extrusion or insulating material typically selected based upon biocompatibility, biostability and durability for the particular application. The insulator material may be silicone, polyurethane, polyethylene, polyamide, polyvinylchloride, PTFE, EFTE, PFA, FEP, or other suitable materials known to those skilled in the art. Alloys or blends of these materials may also be formulated to help control the relative flexibility, torqueability, and pushability of lead 804. In certain embodiments, the insulative material of lead body 806 may be substantially composed of a compliant PURSIL® or CARBOSIL® silicone-urethane copolymer material. In some applications, compliant material characteristic enables the lead body 806 to elongate significant amounts at relatively low stretching forces. Additional descriptions of the insulative materials are described in co-pending U.S. patent application Ser. No. 10/630,376 filed Jul. 29, 2003, entitled "System and Method for Providing A Medical Lead Body Having Conductors That Are Wound in Opposite Directions," and U.S. patent application Ser. No. 10/630,233 filed Jul. 29, 2003, entitled "System and Method for. Providing A Medical Lead Body Having Dual Conductor Layers," the contents of which are herein incorporated by reference in their entirety for all purposes.

As described above in reference to FIGS. 1a through 7b, the distal end 807 (FIG. 8b) of the lead 804 includes a plurality of stimulation electrodes 818 (FIG. 8b). Adjacent to the proximal end 802 of lead 804 may be a plurality of terminals, which in this embodiment, comprises eight connector or terminal electrodes 808. For purposes of illustration only, the lead 804 of FIG. 8a is shown with eight terminals and one "dummy" terminal 809 on the end for assisting with connecting the lead to an implantable impulse generator. As will be appreciated by those skilled in the art, any number of conductors and electrodes may be utilized as desired to form lead 804. Generally, some embodiments have the same number of stimulation electrodes as terminals. In this illustrative embodiment, the terminals are shown as band or ring electrodes.

In certain embodiments, both the stimulation electrodes and the terminals may be formed of biocompatible, conductive materials such as stainless steel, platinum, gold, silver, platinum-iridium, stainless steel, MP35N, or other conductive materials, metals or alloys known to those skilled in the art. The size and shape of the electrodes are generally chosen based upon the desired application. In some embodiments, the terminals may be ring electrodes which encircle portions distal end. Other types, configurations and shapes of electrodes as discussed above or known to those skilled in the art may be used with all embodiments disclosed herein.

One or more conductors 810 extending along a substantial portion of the lead body 806 electrically connects the terminals 808 to the respective stimulation electrodes 818 (FIG. 8*b*) which may be similar to the electrodes discussed in reference to FIGS. 1*a*-7*a*. The conductors of the lead may be maintained in electrical isolation by the insulative material of the lead body 806.

In certain embodiments, the conductors 810 may be formed of a conductive material having desirable characteristics such as biocompatibility, corrosion resistance, flexibility, strength, low resistance, etc. The conductors may take the form of solid wires, drawn-filled-tube (DFT), drawn-brazed-strand (DBS), stranded wires or cables, ribbon conductors, or other forms known or recognized to those skilled in the art. The composition of the conductors may include aluminum, stainless steel, MP35N, platinum, gold, silver, copper, vanadium, alloys, or other conductive materials or metals known to those of ordinary skill in the art. In some embodiments, the number, size, and composition of the conductors will depend on the particular application for the lead, as well as the number of electrodes.

FIG. 8*b* illustrates the lead 804 connected to an implantable pulse generator (IPG) 812 via a receptacle 814. Multiple leads may be coupled to IPG 812 if the header 816 of IPG 812 is so adapted. An example of a commercially available implantable pulse generator is the EON® pulse generator (available from St. Jude Medical Neuromodulation Division). Any of the preceding lead arrangements may be employed with IPG 812.

In this illustrative example, the lead 804 is connected to the implantable pulse generator 812 via a receptacle 814 in a header 816. The lead 804 may be detached from the pulse generator 812 as desired by applying a detaching force and removing the proximal end 802 (FIG. 8*a*) of the lead 804 from the receptacle 814. Similarly, the lead 804 may be connected to the pulse generator 812 by pushing the proximal end 802 into the receptacle 814. A set screw or other locking mechanism (not shown) secures the lead 804 in place within the header 816 and prevents the lead from being dislodged from receptacle 814.

When the system is assembled, the terminals 808 (FIG. 8*a*) are in electrical contact with electrical connectors (not shown) within the header 816 of the pulse generator 812. A plurality of feedthrough wires (not shown) connect the electrical connectors to pulse generating circuitry (not shown) within the pulse generator 812. The pulse generator 812 sends electrical pulses to electrical connectors, which are in electrical contact with the terminals 808. As previously discussed, the terminals 808 are themselves in electrical contact with the stimulation electrodes 818 at distal end 807 of lead 804 because conductors 810 (FIG. 8*a*) electrically connect the terminals 808 to the stimulation electrodes.

Thus, the pulse generator 812 may generate and send electrical pulses via the lead 804 to the stimulation electrodes 818. In use, the stimulation electrodes 818 are placed at a stimulation site (not shown) within a body that is to receive electrical stimulation from the electrical pulses. The stimulation site may be, for example, adjacent to one or more nerves in the central nervous system (e.g., spinal cord). The pulse generator 812 may be capable of controlling the electrical pulses by varying signal parameters (e.g., pulse amplitude, pulse width, pulse frequency, etc.) in response to control signals. In certain embodiments, the pulse generator 812 may programmed by or be in communication with an external programming device (not shown) which supplies the control signals.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

What is claimed is:

1. A paddle-style lead for implantation in the epidural space through an insertion tool, the paddle-style lead comprising:
   a lead body;
   a plurality of conductors extending from a proximal portion of the lead body to a distal portion of the lead body;
   a plurality of terminals that are electrically coupled to the plurality of conductors; and
   a paddle structure that comprises a frame of rigid material, the frame comprising first, second, and third longitudinal members in a planar configuration, a distal linking portion that is mechanically coupled to the first, second, and third longitudinal members, and a proximal linking portion that is mechanically coupled to the first, second, and third longitudinal members;
   wherein a respective plurality of electrodes are provided for each of the first, second, and third longitudinal members, each plurality of electrodes being electrically coupled to conductors of the plurality of conductors;
   wherein the distal and proximal linking portions are adapted to permit compression of the first and third longitudinal members toward each other and to permit the second longitudinal member to move out of plane relative to the first and third longitudinal members when a compressive force is applied to the paddle.

2. The paddle-style lead of claim 1 wherein the distal and proximal linking portions provide a spring-force to restore the first, second, and third longitudinal members to the planar configuration after removal of compressive forces upon the paddle.

3. The paddle-style lead of claim 1 wherein the second longitudinal member comprises a plurality of columns of electrodes along a length of the second longitudinal member.

4. The paddle-style lead of claim 1 wherein the first, second, and third longitudinal members are fabricated using a rigid polymer selected from the group consisting of PEEK, PEKK, and LCP.

5. The paddle-style lead of claim 1 wherein the plurality of electrodes of the first, second, and third longitudinal members are deposited on rigid insulative material of the first, second, and third longitudinal members.

6. The paddle-style lead of claim 1 wherein the plurality of electrodes of the first, second, and third longitudinal members are disposed on an intermediate polymer later that is laminated to a thicker substrate layer.

7. The paddle-style lead of claim 1 wherein electrical connectors are embedded within the first, second, and third longitudinal members and the electrical connectors are electrically coupled to the plurality of electrodes through vias in insulative material.

8. The paddle-style lead of claim 1 wherein the plurality of electrodes of the first, second, and third longitudinal members are provided on one or more flex-circuits that are laminated to rigid insulative material of the first, second, and third longitudinal members.

9. The paddle-style lead of claim 1 wherein the distal linking portion provides a spring force to the paddle to bias the first, second, and third longitudinal members in a planar configuration.

10. The paddle-style lead of claim 1 wherein the proximal linking portion provides a spring force to the paddle to bias the first, second, and third longitudinal members in a planar configuration.

11. A method of fabricating a paddle-style lead for implantation in the epidural space through an insertion tool, the method comprising:
   providing a lead body with a plurality of conductors extending from a proximal portion of the lead body to a distal portion of the lead body;
   forming a paddle structure comprising a frame of rigid material, the frame comprising first, second, and third longitudinal members in a planar configuration, a distal linking portion that is mechanically coupled to the first, second, and third longitudinal members, and a proximal linking portion that is mechanically coupled to the first, second, and third longitudinal members, wherein the distal and proximal linking portions are adapted to permit compression of the first and third longitudinal members toward each other and to permit the second longitudinal member to move out of plane relative to the first and third longitudinal members when a compressive force is applied to the paddle;
   providing a respective plurality of electrodes for each of the first, second, and third longitudinal members; and
   electrically coupling each plurality of electrodes to conductors of the plurality of conductors.

12. The method of claim 11 wherein the distal and proximal linking portions provide a spring-force to restore the first, second, and third longitudinal members to the planar configuration after removal of compressive forces upon the paddle.

13. The method of claim 11 wherein the second longitudinal member comprises a plurality of columns of electrodes along a length of the second longitudinal member.

14. The method of claim 11 wherein the first, second, and third longitudinal members are fabricated using a rigid polymer selected from the group consisting of PEEK, PEKK, and LCP.

15. The method of claim 11 wherein the plurality of electrodes of the first, second, and third longitudinal members are deposited on rigid insulative material of the first, second, and third longitudinal members.

16. The method of claim 11 wherein the plurality of electrodes of the first, second, and third longitudinal members are disposed on an intermediate polymer later that is laminated to a thicker substrate layer.

17. The method of claim 11 wherein electrical connectors are embedded within the first, second, and third longitudinal members and the electrical connectors are electrically coupled to the plurality of electrodes through vias in insulative material.

18. The method of claim 11 wherein the plurality of electrodes of the first, second, and third longitudinal members are provided on one or more flex-circuits that are laminated to rigid insulative material of the first, second, and third longitudinal members.

19. The method of claim 11 wherein the distal linking portion provides a spring force to the paddle to bias the first, second, and third longitudinal members in a planar configuration.

20. The method of claim 11 wherein the proximal linking portion provides a spring force to the paddle to bias the first, second, and third longitudinal members in a planar configuration.

* * * * *